United States Patent
Bakács et al.

(10) Patent No.: US 11,161,903 B2
(45) Date of Patent: *Nov. 2, 2021

(54) LOW DOSE IMMUNE CHECKPOINT BLOCKADE IN METASTATIC CANCER

(71) Applicant: Ralf Kleef, Vienna (AT)

(72) Inventors: Tibor Bakács, Budapest (HU); Ralf Kleef, Vienna (AT)

(73) Assignee: Ralf Kleef, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 16/439,396

(22) Filed: Jun. 12, 2019

(65) Prior Publication Data
US 2019/0292262 A1 Sep. 26, 2019

Related U.S. Application Data

(63) Continuation of application No. 15/443,589, filed on Feb. 27, 2017, now Pat. No. 10,358,496.

(60) Provisional application No. 62/301,643, filed on Mar. 1, 2016.

(51) Int. Cl.
| | |
|---|---|
| A61K 39/395 | (2006.01) |
| C07K 16/28 | (2006.01) |
| A61K 39/00 | (2006.01) |
| A61K 38/20 | (2006.01) |
| A61K 31/549 | (2006.01) |
| A61K 31/675 | (2006.01) |
| C07K 16/30 | (2006.01) |

(52) U.S. Cl.
CPC ........ *C07K 16/2818* (2013.01); *A61K 31/549* (2013.01); *A61K 31/675* (2013.01); *A61K 38/2013* (2013.01); *A61K 39/0008* (2013.01); *A61K 39/00115* (2018.08); *A61K 39/3955* (2013.01); *C07K 16/30* (2013.01); *A61K 2039/505* (2013.01); *A61K 2039/507* (2013.01); *C07K 2317/21* (2013.01); *C07K 2317/24* (2013.01); *C07K 2317/76* (2013.01)

(58) Field of Classification Search
CPC .......... C07K 16/2818; A61K 39/00115; A61K 39/0008; A61K 39/3955
See application file for complete search history.

(56) References Cited

U.S. PATENT DOCUMENTS

| | | | |
|---|---|---|---|
| 9,243,068 B2 | 1/2016 | Evans et al. | |
| 9,402,899 B2 | 8/2016 | Honjo et al. | |
| 9,833,512 B2 | 12/2017 | Hoelzinger et al. | |
| 10,034,924 B2 | 7/2018 | Powell et al. | |
| 10,047,074 B2 | 8/2018 | Cowley et al. | |
| 10,166,273 B2 | 1/2019 | Wittrup et al. | |
| 10,261,083 B2 | 4/2019 | Vasiljeva et al. | |
| 10,350,275 B2 | 7/2019 | Aguilar-Cordova | |
| 10,501,537 B2 | 12/2019 | Wong | |
| 10,583,183 B2 | 3/2020 | Magliocco et al. | |
| 10,682,365 B2 | 6/2020 | Krieg | |
| 2017/0158776 A1 | 6/2017 | Feltquate et al. | |

FOREIGN PATENT DOCUMENTS

WO 2015/0176033 A1 11/2015

OTHER PUBLICATIONS

Wolchok et al.: "Nivolumab plus Ipilimiimab in Advanced Melanoma", New England Journal of Medicine, 2013, vol. 369, No. 2, pp. 122-133.
Postow et al.: "Nivolumab and Ipilimumab versus Ipilimumab in Untreated Melanoma", New England Journal of Medicine, 2015, vol. 372, pp. 2006-2017.
Wolchok et al.: "Ipilimumab monotherapy in patients with pretreated advanced melanoma: a randomised, double-blind, multicentre, phase 2, dose-ranging study", Lancet Oncology, 2010, vol. 11, No. 2, pp. 155-164.
Brahmer et al.: "Safety and Activity of Anti-PD-L1 Antibody in Patients with Advanced Cancer", New England Journal of Medicine, 2012, vol. 366, No. 26, pp. 2455-2465.
Villadolid et al.: "Immune checkpoint inhibitors in clinical practice: update on management of immune-related toxicities", Translational Lung Cancer Research, 2015, vol. 4, No. 5, pp. 560-575.
Philips et al.: "Therapeutic uses of anti-PD-1 and anti-PD-L1 antibodies", International Immunology, 2014, vol. 27, No. 1, pp. 39-46.
Viteri et al.: "Results of clinical trials with anti-programed death 1/programmed death ligand 1 inhibotors in lung cancer"; Translational lung cancer research, 2015, vol. 4(6); pp. 756-762.
Foley et al.: "Current progress in immunotherapy for pancreatic cancer", Cancer Lett., 2016, vol. 381(1), pp. 244-251.
Champiat et al.: "Management of immune checkpoint blockade dysimmune toxicities: a collaborative position paper", Annals of Oncology, 2016, vol. 27, pp. 559-574.

*Primary Examiner* — Robert C Hayes
(74) *Attorney, Agent, or Firm* — Jason D. Voight

(57) ABSTRACT

A method of treating cancer comprising and reducing autoimmune side effects in administration of anti-CTLA-4 antibodies. The invention provides methods for low dose immune checkpoint (IC) treatment of metastatic cancer by delivering anti-CTLA-4 and anti-PD-1 antibodies to cancer patients. Methods also provide for IL-2 stimulation for the activation of T cells against tumor cells. The invention further provides methods for daily cyclic high fever response (hyperthermia) during IL-2 therapy. The methods provide treatment of metastatic cancer without unacceptable autoimmune side effects.

14 Claims, 4 Drawing Sheets

| Rec. No.: | Date | Tumor-associated Marker* [mRNA Copy Number] | | | | | | | |
|---|---|---|---|---|---|---|---|---|---|
| | | KRT19 | MMG | MUC1 | EpCAM | SPDEF | ERBB2 | TERT | CTC-Score |
| 64903 | Mai. 28th 2015 | 2 | (-) | 12 | 2 | 11 | 4 | 7 | 38 |
| 65578 | Nov. 05th 2015 | (-) | (-) | 12 | (-) | 7 | 6 | 15 | 40 |

* KRT19: Cytokeratin-19, MGB1=SCGB2A2, MUC1: Mucine-1, EpCAM: Epithelial Cell adhesion
SPDEF: Ets. Transcriptionfactor, ERBB2: Her2/neu Gene, TERT: Telomerase.
(-): negative/ n.d.: not detected RT-PCR profile of sample date Nov, 05th 2015.

LOW DOSE IMMUNE CHECKPOINT BLOCKADE IN METASTATIC CANCER

This application is a continuation of application Ser. No. 15/443,589, filed Feb. 27, 2017, which claims priority to U.S. Provisional Application Ser. No. 62/301,643, filed Mar. 1, 2016, the entire disclosures of which are incorporated by reference herein.

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

This invention pertains to novel immunological methods related to low-dose immune checkpoint (IC) blockade in metastatic cancer, and methods of administering such antibodies in conjunction with interleukin 2 (IL-2) treatments.

BACKGROUND OF THE INVENTION

Cancer immunotherapy trials conducted with the best available science resulted in anecdotal responses such that the field of cancer immunotherapy did not quite succeed fulfilling the great hopes of conquering cancer and began to lose credibility (Allison, JAMA, 1113-1115 (2015)). In contrast, studies initiated by James P. Allison led to a breakthrough via the immune checkpoint (IC) blockade (Postow et al., J Clin Oncol, 33, 1974-1982 (2015)).

While the CTLA-4 blockade interrupted T cell pathways responsible for immune down-regulation and mediated regression of established malignant tumors in a minority of patients, this has to be weighed against the immune-related adverse events (irAEs) suffered by the majority. The data from 14 completed phase I-III trials of ipilimumab indicated that irAEs occurred in 64.2% of patients. Life-threatening side effects, pathognomonic of acute graft-versus-host-disease (GVHD) and drug-related deaths (<0.1%) have been reported in most trials (Graziani et al., Pharmacological Research, 65, 9-22 (2012)) (Voskens et al., PLoS. ONE., 8, e53745-(2013)) (Shih et al., Drugs, 74, 1993-2013 (2014)). An interesting and consistent observation is that a higher incidence of irAEs, particularly grade 3/4 irAEs, has been associated with a higher proportion of patients eventually achieving an objective response (Attia et al., J Clin Oncol, 23, 6043-6053 (2005)). An increase in the immune-related adverse events is dependent upon the doses (irAEs of any grade 70%, 65%, and 26% of patients at doses of ipilimumab (anti-CTLA-4 antibody) of 10 mg/kg, 3 mg/kg, and 0.3 mg/kg respectively); in the 10 mg/kg patient group, a quarter of the patients suffered grade 3-4 events (Robert et al., Oncologist., 14, 848-861 (2009)). In this context, we addressed the safety-efficacy problem in ipilimumab trials, which is still an unresolved and timely issue in oncology (Bakacs et al., Immunobiology, 217, 583-589 (2012)) (Bakacs et al., Pharmacol. Res., 66, 192-197 (2012)) (Slavin et al., Pharmacol. Res., (2013)) (Bakacs et al., Immunobiology, 220, 624-625 (2014)).

The instant invention suggests a therapeutic paradigm shift, which may help break the impasse. This is based on two groundbreaking but neglected proof-of-principle papers that demonstrated augmented graft-vs.-malignancy (GVM) effect that reversed the relapse of malignancy without worsening the graft-vs.-host disease (GVHD) by a CTLA-4 blockade. The task, in the inventors' view, is not trying to increase dosages of immune-suppressive steroid treatments, but harnessing the immense forces liberated by the anti-CTLA-4 antibody blockade by pre-targeting or dose adjustments.

The main difference between the registered high dose IC blockade (i.e. 3 mg/kg or 10 mg/kg) and our low dose IC blockade (using 0.3 mg/kg) is that only the higher ipilimumab doses were sufficient to translate into an objective response (Wolchok et al., Lancet Oncol, 11, 155-164 (2010)). One recognizes of course that with a higher dose there was a statistically significant trend, indicating a higher best objective response rate (Robert et al., Oncologist., 14, 848-861 (2009)); similarly, patients who received more therapy did better, but had therefore increased risk of developing irAEs. With low dose IC blockade (0.3 mg/kg) no grade 3-4 immune-related adverse events were reported. The appearance of mild-to-moderate immune-related events suggested a biological effect of ipilimumab extending the expiration date of T cells that was however insufficient to translate into an objective response. The latter is achieved with high dose (HD) IL-2 stimulation therapy, which complements the low dose IC blockade. Hyperthermia improves antitumor immune responses by activation of antigen-presenting cells and changes in lymphocyte trafficking.

The first case report describes a stage IV female TNBC patient with far advanced bilateral pulmonary metastasis who exhausted all conventional treatment. However, she went into nearly complete remission with low-dose IC blockade in combination with HD IL-2 treatment under Taurolidine protection and locoregional- and whole body hyperthermia but without classical chemotherapy. This case unexpectedly demonstrates that the liberated autoimmune forces can indeed be safely and effectively harnessed by dose adjustments of the IC blockade.

Breast cancers that lack estrogen receptor (ER) and progesterone receptor (PR) and demonstrate no over expression of human epidermal growth factor receptor 2 (HER2) are referred to as triple-negative breast cancer (TNBC). These tumors belong to the so called basal-like genomic subgroup and have poorer prognosis than the major breast cancer sub-types (Boyle, Annals of Oncology, 23, vi7-vi12 (2012)) (Kassam et al., Clin Breast Cancer, 9, 29-33 (2009)) (Perou et al., Nature, 406, 747-752 (2000)). Based on clinical experience many women with TNBC relapse more frequently and earlier than other subtypes, and continue to progress on administered first-, second-, and third-line palliative chemotherapy. TNBC also have a more aggressive course with shorter disease-free survival and overall survival (OS) times than other breast cancers (Perou et al., Nature, 406, 747-752 (2000)) (Sorlie et al., Proc Natl. Acad. Sci U.S.A, 100, 8418-8423 (2003)). Patients with TNBC have an increased likelihood of distant recurrence, a predilection for visceral, as opposed to bony, sites of relapse and death within 5 years of diagnosis (Andre et al., Ann Oncol, 23 Suppl 6, vi46-vi51 (2012)) (Anders et al., Clin Breast Cancer, 9 Suppl 2, S73-S81 (2009)). Due to the lack of specific targeted therapies increasing interest has been generated in novel treatment strategies in the metastatic setting, which would be essential to improve the survival of this high-risk subgroup (Lehmann et al., J Clin Invest, 121, 2750-2767 (2011)).

The HD IL-2 treatment—typically intravenous bolus of 600,000 or 720,000 Units/kg every 8 hours up to a maximum of 14-15 doses subject to toxicity—was historically one of the few treatments for adults with stage IV solid tumors that could produce complete responses (CRs) often durable for decades without further therapy (Dutcher et al., Journal for Immunotherapy of Cancer, 2, 1-23 (2014)). Twenty years of evolution has led to a plethora of effective management approaches as how to administer the maximum number of doses of IL-2 without putting the patient at unacceptable risk for severe, irreversible toxicity. IL-2 results in a cascade of cytokines released at supra-physiologic levels ('cytokine storm') from IL-2-activated T cells resulting in a well-described vascular leak syndrome (VLS) and eventual end-organ dysfunction.

Both preclinical and clinical data have demonstrated improved antitumor immune responses with the addition of mild hyperthermia. Its molecular mechanisms include the generation of heat shock proteins (Hsps), the activation of antigen-presenting cells and changes in lymphocyte trafficking. In addition, mild, fever range (40° C.) prolonged whole body hyperthermia may help reducing interstitial pressure in the tumor microenvironment (Skitzki et al., Curr Opin Investig. Drugs, 10, 550-558 (2009)) (Repasky et al., Cancer Immunol Res, 1, 210-216 (2013)) (Sen et al., Cancer Res, 71, 3872-3880 (2011)).

SUMMARY OF THE INVENTION

Figure 1A:
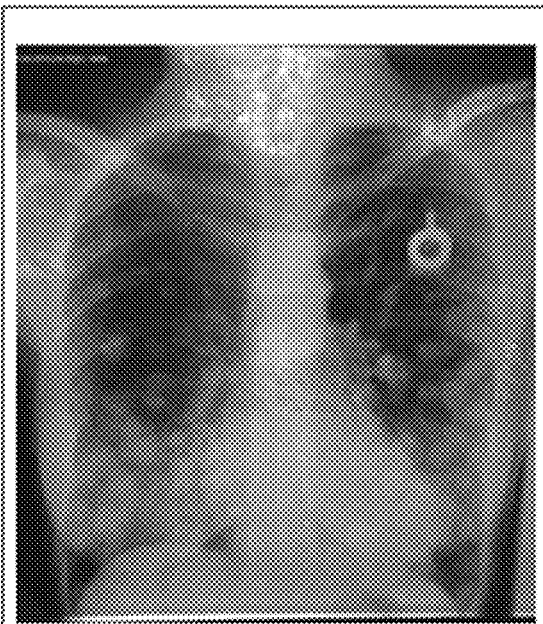
FIGS. 1A to 1D depict a series of classical chest X-ray pictures starting a day after completing the combination therapy. A chest X-ray taken in June 2015 demonstrated far advanced bilateral pulmonary metastatic disease (FIG. 1A) of Case report 1. The second chest X-ray in August, 2015, however, already demonstrated a 20% reduction of lung metastases (FIG. 1B). Two months later, in October 2015, the third chest X-ray demonstrated remarkable further partial remission (FIG. 1C). Six months later the X-ray demonstrated near complete remission (FIG. 1D).
Figure 1B:
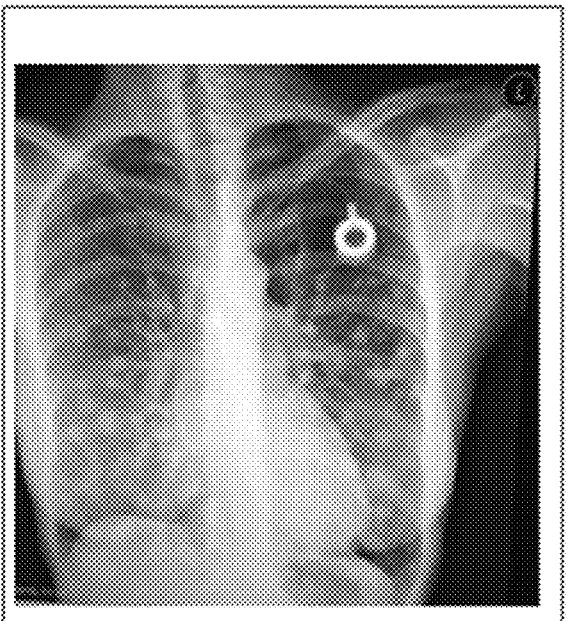
Figure 1C:
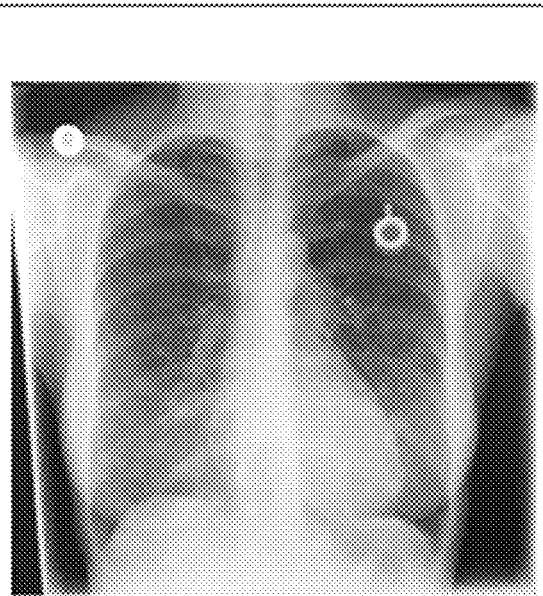
Figure 1D:
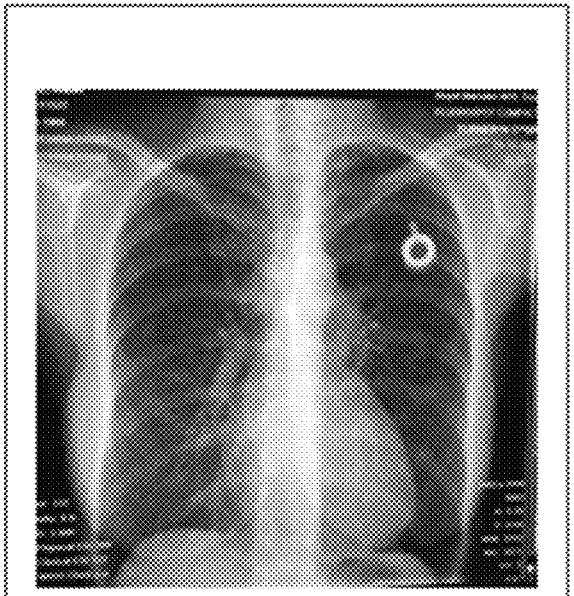

Slavin et al have proposed first that the ipilimumab induced autoimmunity could be safely exploited for augmenting the graft versus malignancy (GVM) effect in high risk patients at the stage of minimal residual disease (MRD) (Slavin et al., Pharmacol. Res., (2013)). This suggestion is based on clinical observations reporting mild-to moderate immune-related events but no grade 3-4 irAEs in the 0.3 mg/kg dose group (which is 33-fold less than that used in the second phase III trial (Wolchok et al., Lancet Oncol, 11, 155-164 (2010))). Slavin et al hypothesized that 0.3 mg/kg dosage would be sufficient to translate into an objective response without unacceptable autoimmune side effects by inducing a prolonged auto-graft-versus-host-disease (auto-GVHD). However, Slavin's method works only in minimal residual disease when the tumor burden is low. The instant invention combines low dose IC blockade with HD IL-2 therapy in order to be effective also in patients with high tumor burden such as in stage IV cancer with advanced pulmonary metastases.

The inventors hypothesized that a prolonged combined low dose IC blockade of two checkpoints, CTLA-4 and PD-1 (using ipilimumab and nivolumab or pembrolizumab or pidilizumab simultaneously; see in (Dolan et al., Cancer Control, 21, 231-237 (2014))) could be safely and effectively administered in patients with high tumor burden provided the IC blockade is complemented with HD IL-2 stimulation treatment. This hypothesis is based on the assumption that a frequently administered low dose (LD) IC blockade would prevent T cell exhaustion enabling them to travel to tumor sites without prematurely succumbing to apoptosis. This would make main stream HD IL-2 stimulation treatment more effective. Consistent with this, autoimmune manifestations (e.g. leukoderma) following HD IL-2 treatment have been associated with a higher therapeutic response rate and a better prognosis in patients at stage III and stage IV melanoma. It should also be noted that vemurafenib and ipilimumab have been associated with leukoderma as a side effect (Gathings et al., Acta Derm. Venereol., 95, 197-200 (2015)).

Unfortunately, due to its severe side effects (particularly the life-threatening vascular leak syndrome (VLS) (Vial et al., Drug Saf, 7, 417-433 (1992)), the highly effective HD IL-2 therapy stimulating the cytotoxic T cell response has never gained widespread acceptance. It was, however, demonstrated that taurolidine potentiates the anti-neoplastic effects of IL-2 while reducing its associated endothelial cell dysfunction in experimental settings (Neary et al., Ann Surg Oncol, 17, 1135-1143 (2010)). More importantly, co-administration of taurolidine with HD rIL-2 in stage IV melanoma patients greatly enhanced the tolerability of this regime by diminishing the VLS without diminishing its therapeutic value (O'Brien et al., Ir. J Med Sci, 175, 10-14 (2006)).

As described above, partial remission was observed two months after the first cycle of immune therapy was finished. This was expected, since disease response was observed after early evidence of disease progression in several studies with CTLA-4 blockade (Hoos et al., J Natl. Cancer Inst., 102, 1388-1397 (2010)). It is realized by now that immune therapies exert their effects on cancer indirectly by building an immune response first, which is then followed by changes in tumor burden or patient survival. The median time to achieve complete response was 30 months. Immune therapy may induce unusual kinetics of antitumor response, which is not captured by Response Evaluation Criteria in Solid Tumors (RECIST) or World Health Organization criteria (Postow et al., J Clin Oncol, 33, 1974-1982 (2015)).

The most common irAE for both CTLA-4 and PD-1 therapy involves dermatologic toxicity, which is also typically the irAE with the earliest onset, within several weeks. Anti-PD-1 induces dermatitis through a separate T cell-mediated mechanism from those typically reported with anti-CTLA-4 treatments (Joseph et al., Cancer Immunol Res, 3, 18-22 (2015)). Dermatologic toxicity was also observed in this patient, but due to the LD IC blockade (0.3 mg/kg and 0.5 mg/kg of ipilimumab and nivolumab, respectively), only very mild of the most clinically relevant irAEs (diarrhea and colitis) occurred, which typically do not present until approximately 6 weeks into treatment after several doses of HD CTLA-4 blockade (3 mg/kg or 10 mg/kg).

It has been demonstrated that the efficacy of different checkpoint inhibitors was improved in combination with chemotherapy in triple negative breast cancer (Bryant et al., BMC. Cancer, 14, 570-(2014)). Chemotherapy drugs and irradiation have been reported helpful in breaking immune tolerance and creating the tumor-microenvironment for adoptive cell therapy. The reason for this is that low-dose cyclophosphamide or gemcitabine therapy can selectively deplete T regulatory cells (Treg). Paclitaxel can alter cytokine network at the tumor site, and 5-fluorouracil shows a pronounced effect on myeloid-derived suppressor cells (MDSC) depletion. Local tumor irradiation and total body irradiation (TBI) can also affect tumor microenvironment and facilitate immunotherapy (Ouyang et al., Tumour. Biol, (2015)) (Zheng et al., Cell Immunol, 294, 54-59 (2015)).

In summary, to our knowledge, this is the first reported case of a stage IV TNBC patient with far advanced pulmonary metastases who underwent nearly complete remission by receiving simultaneously LD anti-CTLA-4 and anti-PD-1 antibodies (ipilimumab and nivolumab) in combination with HD IL-2 treatment and hyperthermia. Importantly, the feasibility and safety of this multidisciplinary treatment approach was demonstrated using immune based therapies without conventional cytotoxic chemotherapy.

DETAILED DESCRIPTION OF THE EMBODIMENT

Examples

Case Report 1

In September 2013, a fifty year old Caucasian female [AW, Jun. 9, 1964.] presented at The Royal Marsden Cancer Charity Hospital, London, with a histologically confirmed invasive ductal carcinoma of the right breast measuring 3 cm, and axillary involvement (C5). The tumor displayed medullary features and grade 3 (G3) morphology according to Nottingham grading system. The molecular biology profile was ER, PR and Her2 negative (TNBC [ICD10: C50.9]) with a Ki-67 index of 61%; additional evidence of a ductal carcinoma in situ (DCIS) with local vascular invasion was also obtained. The BRCA1 mutation analysis proved to be negative. In November and December 2013, the patient underwent neoadjuvant Taxol chemotherapy (consisting of eight weekly cycles). Due to peripheral neuropathy Taxol had to be changed to neoadjuvant epirubicin and cyclophosphamide (EC) combination chemotherapy (four weekly cycles). In May 2014, a lumpectomy was carried out with wide local excision together with sentinel biopsy, which were negative (0/2), pT3, pN0, MO, G3, RO. Six months later, however, a repeated axillary lymph node biopsy demonstrated metastatic dissemination to the axillary lymph nodes. In August 2014, the patient underwent adjuvant radiotherapy of the right chest wall with 40 Gy in 15 fractions and additionally 13.35 Gy in 5 fractions. In February, 2015 right axillary multiple lymph node metastases up to 1.2 cm [ICD10: R59.1] and disseminated pulmonary metastases up to 2 cm in size were detected without pleural effusions [ICD10: C78.6]. The neutropenia of the patient had to be treated with G-CSF support. A whole body bone scan scintigraphy proved to be unremarkable in April 2015.

The patient first presented at the Immunology & Integrative Oncology clinic, Vienna, in May 2015, with a 80% of Karnofsky score (ECOG=1), mild neuropathy with distal predominance in all four extremities. During inspiration the patient felt severe pain in the left lateral chest wall, which became extremely painful during sneezing. She complained about severe shortness of breath (SOB) on exertion, lack of appetite, insomnia, and exhaustion.

All clinical studies were approved by the Immunology & Integrative Oncology Institutional Review Board (IRB). After extensive informed consent and careful review of the organ systems a combined immunotherapy and hyperthermia was initiated. In June 2015, the patient underwent a four-week combination of HD IL-2 with LD IC therapy as follows. A low-dose PD-1 IC inhibitor nivolumab (0.5 mg/kg) with CTLA-4 IC inhibitor ipilimumab (0.3 mg/kg) was administered weekly, over three weeks. This was accompanied by locoregional hyperthermia with radiofrequency fields (13.56 MHz) using the Syncrotherm device 3 times per week (max output 400 w) over the thoracic region in combination with high dose vitamin C (0.5 g/kg) and alpha lipoic acid (600 mg) over three weeks. Then, this was followed by long duration fever range whole body hyperthermia in combination with low dose chemotherapy using cyclophosphamide 300 mg/m$^2$ to down modulate Treg cells. Then, a HD IL-2 (54 Mio/m2 as decrescendo regime) therapy under Taurolidine protection was administered for five days.

Figure 2:
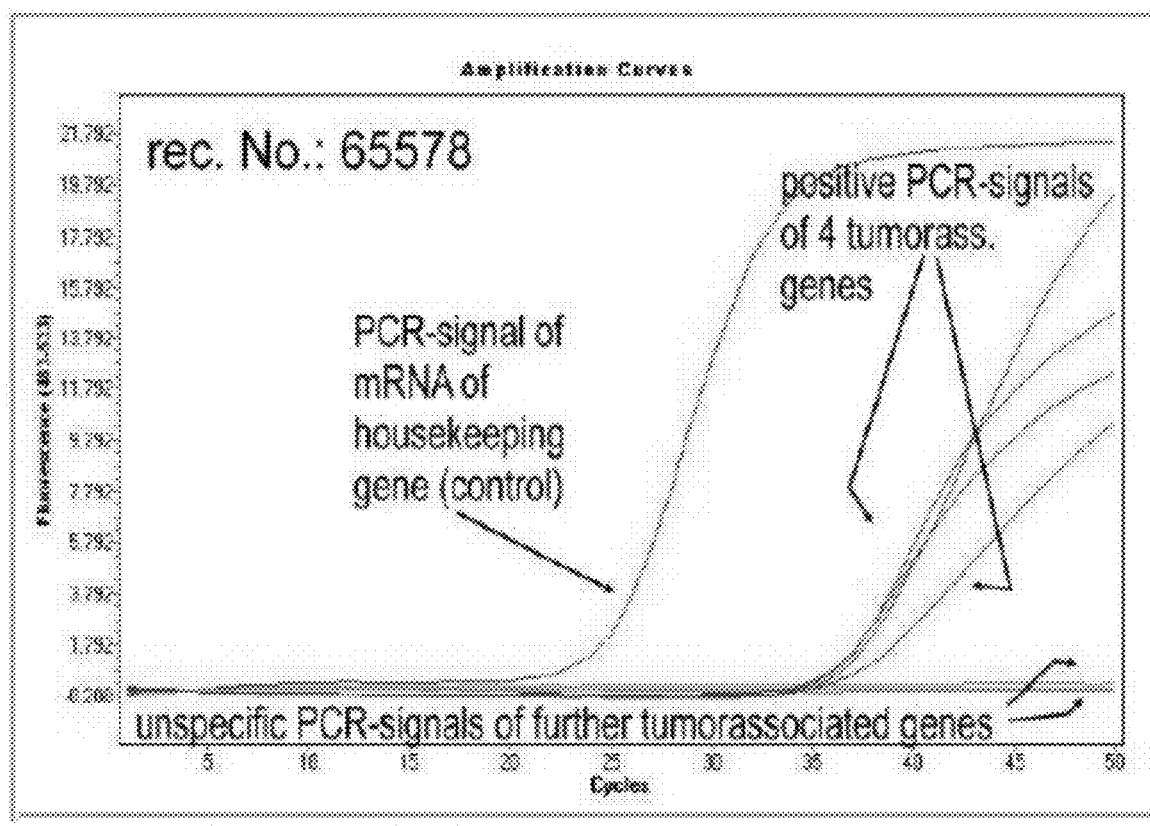
FIG. 2 depicts the analysis of Circulating Tumor Cells "CTC" in Blood indicating stable CTC of Case report 1. Using a modified test system for detection of tumor-specific gene expression by qPCR as a measure of the presence of CTCs the EDTA-Blood-sample was analyzed. Circulating epithelial cells were enriched by immune-magnetic separation and selected tumor-specific genes and a separate housekeeping gene were quantified by qPCR.
Figure 3:
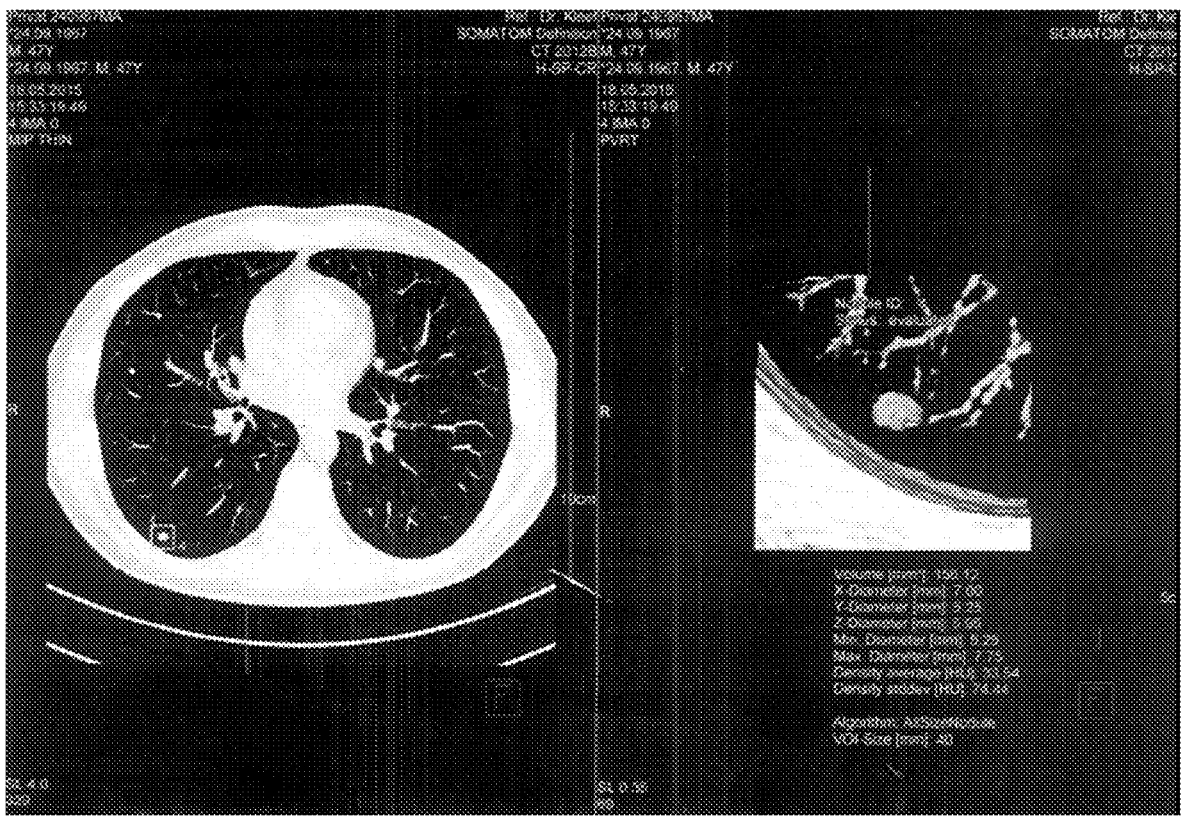
FIG. 3 depicts a CT staging result of Case report 2, lung metastasis from malignant melanoma October 2015 demonstrated partial remission of lung metastasis and interestingly some progression of mediastinal and right internal mammary chain lymph nodes. Radiologically this was interpreted as pseudo-progression, a radiological and clinical phenomenon increasingly reported following immunotherapy with checkpoint inhibitors.
Figure 3:
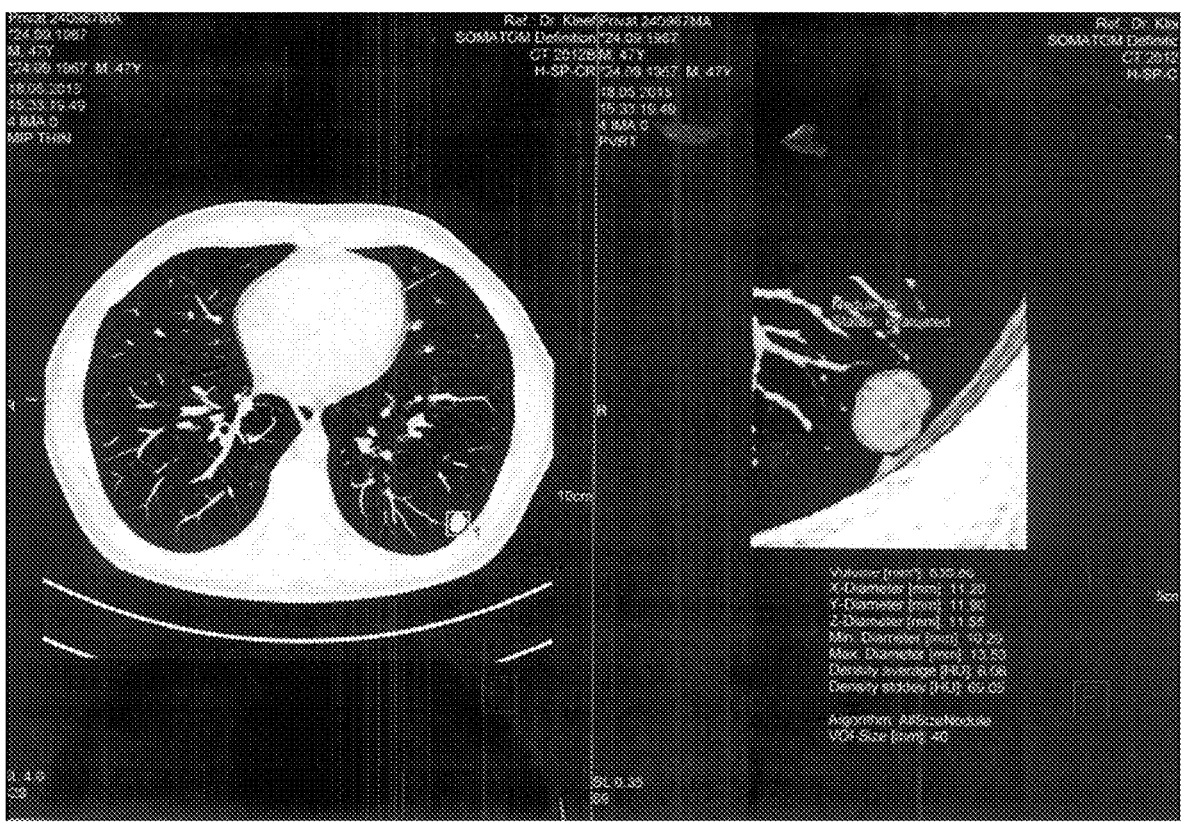
Figure 4:
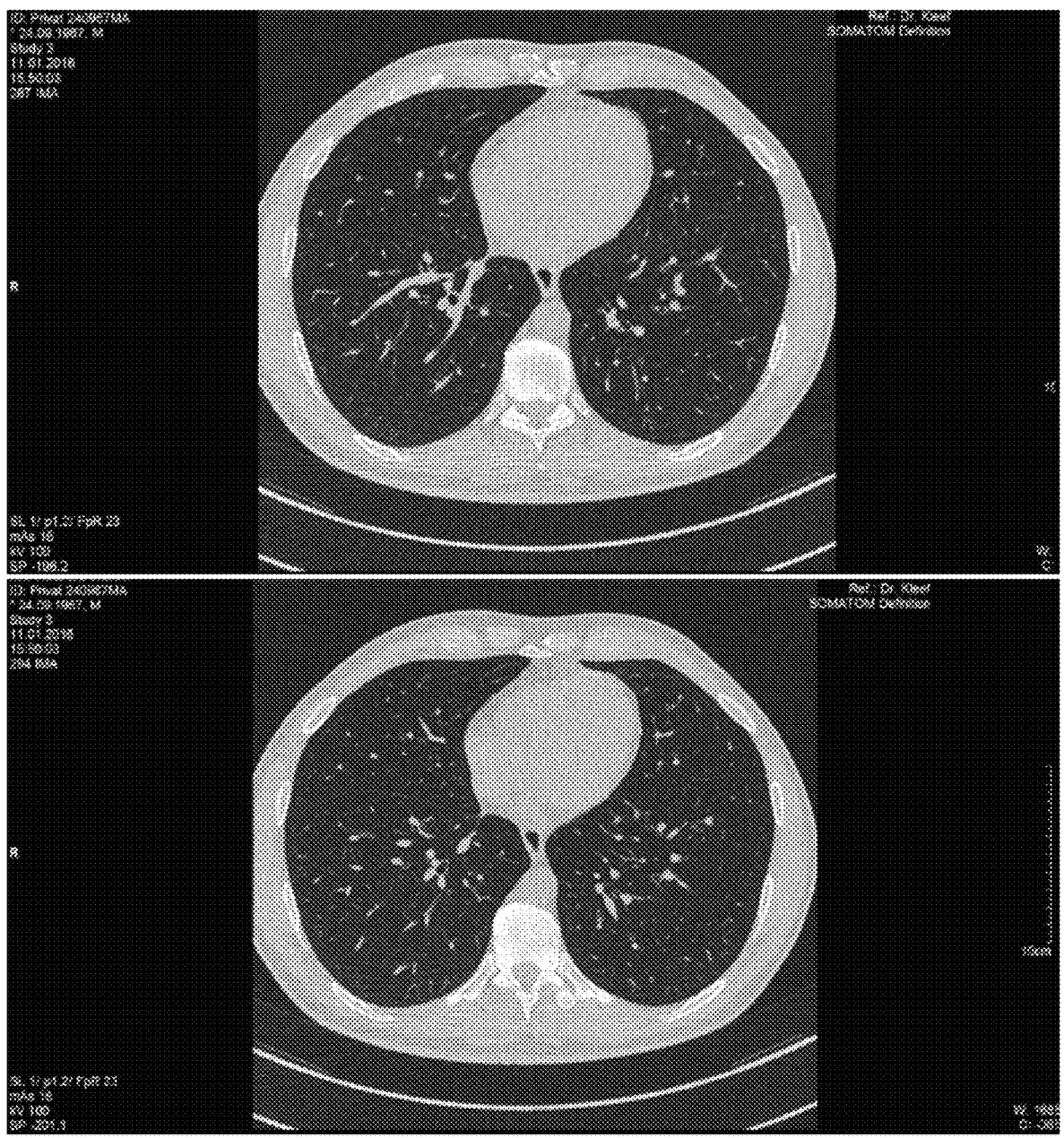
FIG. 4 depicts CT staging result of Case report 2, lung metastasis from malignant melanoma January 2016 indicating complete remission.

A day after completing the combination therapy a classical chest X-ray was taken in order to avoid radiation overload by repeated CT scans. X-ray demonstrated far advanced bilateral pulmonary metastatic disease (see FIG. 1.A). The second chest X-ray in August, 2015, however, already demonstrated a 20% reduction of lung metastases (see FIG. 1.B). Two months later, in October 2015, the third chest X-ray demonstrated remarkable further partial remission (PR) (see FIG. 1.C). Six month later the X-ray demonstrated near complete remission (CR) (see FIG. 1.D). A CT of the thorax, abdomen and pelvis [dated October 2015] also demonstrated this partial remission of lung metastasis and interestingly some progression of mediastinal and right internal mammary chain lymph nodes (see FIG. 2). Radiologically this has to be interpreted as pseudo progression (Michaels et al., Insights. Imaging, (2015)), a radiological and clinical phenomenon increasingly reported following immunotherapy with checkpoint inhibitors (de et al., Cancer Immunol Res, 4, 12-17 (2016)). Importantly, this is associated with an excellent clinical condition with a Karnofsky score of 100%. SOB on exertion or any other cancer related symptoms have vanished. Currently (February 2016) the patient reports excellent health and no cancer related symptoms.

Case Report 2

In February 2015 a 47-year-old Caucasian male presented to our clinic with the diagnosis of pulmonary metastasis from malignant melanoma (ICD C43.0 and ICCCDDD C78.0). Initially, the origin of the primary tumor could not be found and the patient had undergone histological confirmation of 2 lung metastasis both in the left and right lower lobe with 11 and 9 mm respectively. Both lesions displayed increased PET/CT standardized uptake value (SUV) of up to 3.65; the primary lesion later was confirmed in the left cheek which initially had an increased SUV of 4.53. BRAF gene mutation was negative, the melanoma was histologically S100 positive, HMB-45 positive, AE 1/3 negative. Clinically, the patient had a Karnofsky score of 100% and felt no symptoms from the lung metastasis.

Interestingly, initially we only used HD IL-2 therapy which only resulted in stable disease (SD) of the patient with radiological proof of stable lung metastasis. Only when we started combining low-dose checkpoint inhibitor therapy followed by high dose IL-2 therapy the patient went into complete remission. The patient underwent 3 treatment cycles of single high dose IL-2 therapy between February-April 2015.

The patient was switched to the combination of LD IC therapy followed by HD IL-2 in July 2015. The patient underwent the same treatment cycle as described in Case Report 1 using the combination of low-dose IC inhibitors in combination with HD IL-2 and hyperthermia as described in detail also in Case Report 1. Importantly, in August 2015 the patient went on to maintenance therapy with nivolumab 2 mg/kg as mono therapy. A final restaging with CT of the thorax from January 2016 proved complete remission (CR) and only scarring in the area of the previously diagnosed two lung metastasis in the right and left lower lobe. Currently (February 2016) the patient reports excellent health and no cancer related symptoms.

Case Report 3

A 62-year-old Caucasian male with a history of Bladder Carcinoma ICD10: C67.9, bone metastasis ICD10: C79.5 and large local recurrence first presented to our outpatient department in July 2015. The first diagnosis (FD) was November 2009 status post TUR-Bladder and a single BCG instillation (discontinuation due allergic reaction to BCG) *Bacillus* Calmette-Guérin (form of immunotherapy for bladder cancer where this bacteria is instilled in the bladder to stimulate immune system in the bladder epithelium).

April 2015 FD of recurrence/metastasis of bladder tumor right iliacal-inguinal femoral with a PET CT confirmed typical malignancy enrichment; no distant metastases. MRI showed large, right lateral the bladder infiltrating tumor with additional infiltration of acetabulum and os pubis expanded to inguinal and femoral; the primary recurrence had a size of 7×6 cm with suspicious neighboring lymph nodes.

Introduction of a second-line treatment with palliative chemo-radiation in Munich GD 50 Gy and 10 Gy boost to the tumor with Cisplatin weekly 40 mg/m2 in total 6 times on day 1, 8, 15, 22, 29, 36;

When the patient presented to our clinic he had finished radiation and had a Karnofsky score of 70%, constipation, (probably morphine induced), pain VAS 3 in the region of the anterior superior iliac spine radiating to the right trochanter. The patient needed strong morphine medication for pain control.

The patient underwent only one time the same treatment cycle like Case Report 1 using the combination of low-dose IC inhibitors in combination with HD IL-2 and hyperthermia as described in detail in Case Report 1. Only, locoregional hyperthermia was used in the area of the small pelvis.

Like in Case Report 1 immediately following this treatment the patient underwent MRI of the small pelvis which described advanced disease as follows: There was a massive and diffuse bone lesion in the whole ramus superior of the right os pubis including the adjacent parts of the right acetabulum indicating metastatic infiltration. There was necrosis in the middle of the os pubis of 3 cm. Strong suspicion of pathological fissure with neoplastic infiltration in the ramus inferior of the right os pubis with transversal fissure. There was diffuse oedema of the paraosseous musculature strongly suspicious for new neoplastic infiltration.

Additionally, there was a lesion in the area of the left spina iliaca posterior suspicious for incipient metastasis.

October 2015 restaging with CT of the thorax and abdomen with IV contrast demonstrated near complete remission (CR) of the previously described large tumor in the right pelvis and sclerosing of the previously described osteolytic infiltration of the os ileum and the right acetabulum. Importantly, the patient was free of any cancer related symptoms from this time point on. Only lymphatic edema due to previous radiation therapy clinically was a problem in the right lower extremity. It should be mentioned that this patient also received treatment with denosumab from September 2015 on. Currently (February 2016) the patient reports excellent health and no cancer related symptoms.

Case Report 4

A 52-year-old Caucasian male with a history of very far advanced prostate cancer ICD10: C61.0, bone metastasis with ICD10: C79.5 and malignant lymph adenopathy ICD 10: R59.1 first presented to our outpatient department in October 2015.

First diagnosis of the prostate cancer was May 2014 T3a L0 when the patient underwent radical retrocolic prostatectomy including pelvic lymphadenectomy pT3a L0 V0 pN1 (4/20) R0, Gleason score 9. In June 2014 he underwent adjuvant hormone therapy with Casodex 150 mg and LH/RH Analoga with Trenatone until October 2015 when he was switched to an alternative hormone therapy with Diethylstilbestrol (DES) 1 mg.

February 2015 a PET CT with GA 68-PSMA demonstrated greatly enhanced SUV of 20.8 indicating a local recurrence in the prostate loge, retrocolic paravesical SUV enhancement of 6.3, additionally small LK lateral right the common iliac artery at the level SWK 1 SUV 4; additionally small LK lateral to the left common iliac artery at the level base plate L5 SUV 18.3; otherwise unremarkable findings in particular skeletal system.

February-April 2015 starting after percutaneous radiotherapy of pelvic lymphatics on both sides as well as prostate bed with 50 Gy followed by saturation of the prostate bed at 68 Gy and subsequent Cyberknife radiotherapy.

May 2015 PD demonstrated in restaging with CT abdomen with evidence of left para-aortic lymph node metastases to 2 cm size in height of the left renal hilum.

Jul. 9, 2015 State after salvage laparoscopic lymphadenectomy (n=37) with Da Vinci method with subsequent injury of the left ureter with postoperative formation of a 17 cm Urinoma supplied with double J stens.

October 2015 massive PD in PET CT with now multiple PSMA positive lymph node metastasis paraaortal left retrocrural, mediastinal and supraclavicular both sides. SUV 58! In addition, several left-PSM A positive pulmonary metastases and 2 small osseous metastases focally second rib on the right and medial portion of the left clavicle.

The patient presented with a Karnofsky score of 70%, achiness throughout the abdomen most likely caused by lymphadenopathy, constipation, the patient had weight loss of 25 kg indicating the onset of severe cachexia. PSA was 434 ng/mg.

Additionally, the patient was started on 3-weekly chemotherapy with Taxotere according to S3 guidelines.

October-December 2015 the patient underwent only two time the same treatment cycle like Case report 1 using the combination of low-dose IC inhibitors in combination with HD IL-2 and hyperthermia as described in detail in Case Report 1. Only, locoregional hyperthermia was used in the area of the abdomen.

Although currently (February 2016) there is no new restaging with CT or MRT available there is clear proof of a dramatic clinical improvement: The PSA value dropped from 434 ng/mg to 5.7 ng/ml. The patient gained minimum 12 kg of weight and is free from any cancer related symptoms with a Karnofsky score of 100%.

The invention is further described by the following numbered paragraphs:

1. A method of treating cancer comprising administering to a patient in need of anti-PD-1 antibody and anti-CTLA-4 antibody in amounts effective to produce an anti-cancer effect, wherein the administration of anti-PD-1 antibody and anti-CTLA-4 antibody results in a lower level of autoimmunity as compared to administration of either anti-CTLA-4 or anti-PD-1 antibody alone.
2. A method for reducing autoimmune side effects in administration of anti-CTLA-4 antibodies by administering an effective amount of anti-PD-1 antibody to a patient anticipating or experiencing anti-CTLA-4 autoimmune side effects.
3. A method for reducing autoimmune side effects in administration of anti-CTLA-4 antibodies by administering an effective amount of anti-CTLA-4 antibody to a patient anticipating or experiencing anti-PD-1 autoimmune side effects.
4. A method for enhancing cancer immunity in a patient while reducing autoimmunity in said patient comprising administering anti-PD-1 antibody and anti-CTLA-4 antibody in effective amounts to a patient in need of treatment.
5. The method according to any of paragraph 1 to 4, wherein of treating cancer comprising administering to a patient in need co-administration of Taurolidine with HD IL-2.
6. The method according to any of paragraph 1 to 5, wherein of treating cancer by administering to a patient in need of hyperthermia.
7. The method according to any of paragraph 1 to 6, wherein of treating cancer comprising administering to a patient in need 0.5 mg/kg or lower dose of anti-PD-1 antibody with co-administration of 0.3 mg/kg or lower dose of anti-CTLA-4 antibody.
8. The method according to any of paragraph 1 to 7, wherein of treating cancer comprising administering to a patient in need of 300 mg/m2 or lower dose of cyclophosphamide.
9. The method according to any of paragraph 1 to 8, wherein the anti-cancer effect is an effect chosen from decreased tumor burden, decreased metastasis, decreased tumor growth, and reduction in new tumor formation.
10. The method according to any of paragraph 1 to 8, wherein the anti-PD-1 antibody and anti-CTLA-4 antibody are administered simultaneously.
11. The method according to any of paragraph 1 to 8, wherein the anti-PD-1 antibody and anti-CTLA-4 antibody are administered at different times.
12. A composition for treating cancer comprising effective amounts of anti-PD-1 antibody and anti-CTLA-4 antibody, and at least one pharmaceutically acceptable excipient, wherein the amount of the antibodies in the composition is sufficient to produce a lower level of autoimmunity as compared to a composition of either antibody alone.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

Abbreviations

| | |
|---|---|
| CTLA-4 or CTLA4 | Cytotoxic T-lymphocyte-associated Protein 4; target for ipilimumab on immune cells |
| CR | Complete remission |
| CT | Computer tomogram for radiological staging |
| cyclophosphamide | Chemotherapy used in low dose to down-modulate Treg cells |
| denosumab | Drug licensed for the treatment of bone metastasis and important inhibitor of Rank-L |
| ECOG Performance Status | International classification system for disease stage |
| HD IL-2 therapy | High dose IL-2 therapy |
| HMB-45 | human melanoma black 45, melanoma tumor marker |
| ipilimumab | anti-CTLA-4 antibody |
| Karnofsky score | International classification system for disease stage |
| LD IC inhibitor therapy | Low-dose immune checkpoint inhibitor therapy |
| MRI | Magnetic Resonance Imaging |
| MRT | Magnetic resonance tomogram for radiological staging |
| neoadjuvant | Administration of therapeutic agents before a main treatment |
| nivolumab | anti-PD-1 antibody |
| PD | Progressive disease |
| PD-1 or PD-L1 | Programmed cell death protein 1 or Programmed death-ligand 1; target for nivolumab on immune and tumor cells |
| PET | Positron emission tomography |
| PR | Partial remission |
| Rank-Ligand | Receptor activator of nuclear factor kappa-B ligand and important molecule involved in the metabolic control of bone growth and reduction |
| S100 | Melanoma tumor marker |
| SD | Stable disease |
| SUV | Standard uptake value measuring glucose metabolism of cancer cell in PET |
| Syncrotherm | Locoregional hyperthermia with radiofrequency fields (13.56 MHz) |
| Treg cells | T regulatory cells known to be involved in immunosuppression |
| VAS | Visual analogue scale |
| VLS | Vascular leak syndrome |

DOCUMENTS SITED HEREIN ABOVE

1. Allison, J. P., Immune Checkpoint Blockade in Cancer Therapy: The 2015 Lasker-DeBakey Clinical Medical Research Award. JAMA, 1113-1115 (2015).
2. Postow, M. A., Callahan, M. K., and Wolchok, J. D., Immune Checkpoint Blockade in Cancer Therapy. J Clin Oncol, 33, (17): 1974-1982 (2015).
3. Graziani, G., Tentori, L., and Navarra, P., Ipilimumab: A novel immunostimulatory monoclonal antibody for the treatment of cancer. Pharmacological Research, 65, (1): 9-22 (2012).
4. Voskens, C. J. et al., The price of tumor control: an analysis of rare side effects of anti-CTLA-4 therapy in metastatic melanoma from the ipilimumab network. PLoS. ONE., 8, (1): e53745- (2013).
5. Shih, K., Arkenau, H. T., and Infante, J. R., Clinical impact of checkpoint inhibitors as novel cancer therapies. Drugs, 74, (17): 1993-2013 (2014).

6. Attia, P. et al., Autoimmunity correlates with tumor regression in patients with metastatic melanoma treated with anti-cytotoxic T-lymphocyte antigen-4. J Clin Oncol, 23, (25): 6043-6053 (2005).
7. Robert, C. and Ghiringhelli, F., What is the role of cytotoxic T lymphocyte-associated antigen 4 blockade in patients with metastatic melanoma? Oncologist., 14, (8): 848-861 (2009).
8. Bakacs, T., Mehrishi, J. N., and Moss, R. W., Ipilimumab (Yervoy) and the TGN1412 catastrophe. Immunobiology, 217, (6): 583-589 (2012).
9. Bakacs, T. et al., Interesting possibilities to improve the safety and efficacy of ipilimumab (Yervoy). Pharmacol. Res., 66, (2): 192-197 (2012).
10. Slavin, S., Moss, R. W., and Bakacs, T., Control of minimal residual cancer by low dose ipilimumab activating autologous anti-tumor immunity. Pharmacol. Res., (2013).
11. Bakacs, T. and Mehrishi, J. N., Anti-CTLA-4 therapy may have mechanisms similar to those occurring in inherited human CTLA4 haploinsufficiency. Immunobiology, 220, 624-625 (2014).
12. Wolchok, J. D. et al., Ipilimumab monotherapy in patients with pretreated advanced melanoma: a randomised, double-blind, multicentre, phase 2, dose-ranging study. Lancet Oncol, 11, (2): 155-164 (2010).
13. Boyle, P., Triple-negative breast cancer: epidemiological considerations and recommendations. Annals of Oncology, 23, (suppl 6): vi7-vi12 (2012).
14. Kassam, F. et al., Survival outcomes for patients with metastatic triple-negative breast cancer: implications for clinical practice and trial design. Clin Breast Cancer, 9, (1): 29-33 (2009).
15. Perou, C. M. et al., Molecular portraits of human breast tumours. Nature, 406, (6797): 747-752 (2000).
16. Sorlie, T. et al., Repeated observation of breast tumor subtypes in independent gene expression data sets. Proc Natl. Acad. Sci U.S.A, 100, (14): 8418-8423 (2003).
17. Andre, F. and Zielinski, C. C., Optimal strategies for the treatment of metastatic triple-negative breast cancer with currently approved agents. Ann Oncol, 23 Suppl 6, vi46-vi51 (2012).
18. Anders, C. K. and Carey, L. A., Biology, metastatic patterns, and treatment of patients with triple-negative breast cancer. Clin Breast Cancer, 9 Suppl 2, S73-S81 (2009).
19. Lehmann, B. D. et al., Identification of human triple-negative breast cancer subtypes and preclinical models for selection of targeted therapies. J Clin Invest, 121, (7): 2750-2767 (2011).
20. Dutcher, J. P. et al., High dose interleukin-2 (Aldesleukin)—expert consensus on best management practices-2014. Journal for Immunotherapy of Cancer, 2, (26): 1-23 (2014).
21. Skitzki, J. J., Repasky, E. A., and Evans, S. S., Hyperthermia as an immunotherapy strategy for cancer. Curr Opin Investig. Drugs, 10, (6): 550-558 (2009).
22. Repasky, E. A., Evans, S. S., and Dewhirst, M. W., Temperature matters! And why it should matter to tumor immunologists. Cancer Immunol Res, 1, (4): 210-216 (2013).
23. Sen, A. et al., Mild elevation of body temperature reduces tumor interstitial fluid pressure and hypoxia and enhances efficacy of radiotherapy in murine tumor models. Cancer Res, 71, (11): 3872-3880 (2011).
24. Dolan, D. E. and Gupta, S., PD-1 pathway inhibitors: changing the landscape of cancer immunotherapy. Cancer Control, 21, (3): 231-237 (2014).
25. Gathings, R., Lewallen, R., and Yosipovitch, G., Immunotherapy-induced leukoderma from treatment of melanoma with IL-2: a case report and a review of the literature. Acta Derm. Venereol., 95, (2): 197-200 (2015).
26. Vial, T. and Descotes, J., Clinical toxicity of interleukin-2. Drug Saf, 7, (6): 417-433 (1992).
27. Neary, P. M. et al., The evolving role of taurolidine in cancer therapy. Ann Surg Oncol, 17, (4): 1135-1143 (2010).
28. O'Brien, G. C. et al., Co-immunotherapy with interleukin-2 and taurolidine for progressive metastatic melanoma. Ir. J Med Sci, 175, (1): 10-14 (2006).
29. Hoos, A. et al., Improved endpoints for cancer immunotherapy trials. J Natl. Cancer Inst., 102, (18): 1388-1397 (2010).
30. Joseph, R. W. et al., Lichenoid dermatitis in three patients with metastatic melanoma treated with anti-PD-1 therapy. Cancer Immunol Res, 3, (1): 18-22 (2015).
31. Bryant, C., Rawlinson, R., and Massey, A. J., Chk1 inhibition as a novel therapeutic strategy for treating triple-negative breast and ovarian cancers. BMC. Cancer, 14, 570-(2014).
32. Ouyang, Z. et al., Regulatory T cells in the immunotherapy of melanoma. Tumour. Biol, (2015).
33. Zheng, Y. et al., Using chemo-drugs or irradiation to break immune tolerance and facilitate immunotherapy in solid cancer. Cell Immunol, 294, (1): 54-59 (2015).
34. Kleef, R. et al., Fever, Cancer Incidence and Spontaneous Remissions. Neuroimmunomodulation, 9, (2): 55-64 (2001).
35. Michaels, A. Y. et al., Systemic treatment in breast cancer: a primer for radiologists. Insights. Imaging, (2015).
36. de, V. G. et al., Radiologic Heterogeneity in Responses to Anti-PD-1/PD-L1 Therapy in Metastatic Renal Cell Carcinoma. Cancer Immunol Res, 4, (1): 12-17 (2016).

What is claimed is:

1. A method for reducing autoimmune side effects by administering 0.5 mg/kg or lower dose of anti-PD-1 antibody in combination with co-administration of 0.3 mg/kg or lower dose of anti-CTLA-4 antibody to a patient anticipating or experiencing anti-PD-1 or anti-CTLA-4 autoimmune side effects, wherein the anti-CTLA-4 antibody is ipilimumab and the anti-PD-1 antibody is nivolumab, pembrolizumab or pidilizumab, and wherein the patient is being treated with hyperthermia.

2. The method of claim 1 for reducing autoimmune side effects in administration of anti-CTLA-4 antibody by administering an effective amount of anti-PD-1 antibody to a patient anticipating or experiencing anti-CTLA-4 autoimmune side effects.

3. The method of claim 1 for reducing autoimmune side effects in administration of anti-PD-1 antibody by administering an effective amount of anti-CTLA-4 antibody to a patient anticipating or experiencing anti-PD-1 autoimmune side effects.

4. The method of claim 1, further comprising administering Taurolidine to the patient, wherein the patient is being treated with high dose interleukin-2 (HD IL-2).

5. The method of claim 1, comprising administering to the patient in need 0.5 mg/kg or lower dose of anti-PD-1 antibody with co-administration of 0.3 mg/kg or lower dose of anti-CTLA-4 antibody weekly, over three weeks.

6. The method of claim 1, comprising administering to the patient in need 300 mg/m$^2$ or lower dose of cyclophosphamide.

7. A method for enhancing cancer immunity in a patient while reducing autoimmunity in said patient comprising administering 0.5 mg/kg or lower dose of anti-PD-1 antibody and 0.3 mg/kg or lower dose of anti-CTLA-4 antibody to a patient in need of treatment, wherein the anti-CTLA-4 antibody is ipilimumab and the anti-PD-1 antibody is nivolumab, pembrolizumab or pidilizumab, and wherein the patient is being treated with hyperthermia.

8. The method of claim 7, further comprising administering Taurolidine to the patient, wherein the patient is being treated with high dose interleukin-2 (HD IL-2).

9. The method of claim 7, comprising administering to the patient in need 0.5 mg/kg or lower dose of anti-PD-1 antibody with co-administration of 0.3 mg/kg or lower dose of anti-CTLA-4 antibody weekly, over three weeks.

10. The method of claim 7, comprising administering to the patient in need 300 mg/m$^2$ or lower dose of cyclophosphamide.

11. The method of claim 7, wherein the anti-PD-1 antibody and anti-CTLA-4 antibody are administered simultaneously.

12. The method of claim 7, wherein the anti-PD-1 antibody and anti-CTLA-4 antibody are administered at different times.

13. The method of claim 7 comprising administering to a patient in need anti-PD-1 antibody and anti-CTLA-4 antibody in amounts effective to produce an anti-cancer effect, wherein the administration of anti-PD-1 antibody and anti-CTLA-4 antibody results in a lower level of autoimmunity as compared to administration of either anti-CTLA-4 or anti-PD-1 antibody alone.

14. The method of claim 13, wherein the anti-cancer effect is an effect chosen from decreased tumor burden, decreased metastasis, decreased tumor growth, and reduction in new tumor formation.

* * * * *